(12) United States Patent
Dixon (10) Patent No.: US 11,745,359 B2
(45) Date of Patent: Sep. 5, 2023

(54) QUICK RELEASE COUPLER

(71) Applicant: THINK SURGICAL, INC., Fremont, CA (US)

(72) Inventor: Mark Dixon, Fremont, CA (US)

(73) Assignee: Think Surgical, Inc., Fremont, CA (US)

( * ) Notice: Subject to any disclaimer, the term of this patent is extended or adjusted under 35 U.S.C. 154(b) by 0 days.

(21) Appl. No.: 17/718,577

(22) Filed: Apr. 12, 2022

(65) Prior Publication Data

US 2022/0234216 A1 Jul. 28, 2022

Related U.S. Application Data

(63) Continuation-in-part of application No. 16/467,756, filed on Jun. 7, 2019, now Pat. No. 11,312,023.

(60) Provisional application No. 62/433,373, filed on Dec. 13, 2016.

(51) Int. Cl.
*B25J 15/04* (2006.01)
*A61B 17/00* (2006.01)
*A61B 34/00* (2016.01)

(52) U.S. Cl.
CPC ........... *B25J 15/0408* (2013.01); *A61B 17/00* (2013.01); *A61B 34/70* (2016.02); *A61B 2017/00477* (2013.01)

(58) Field of Classification Search
CPC .................................................... B25J 15/0408
See application file for complete search history.

(56) References Cited

U.S. PATENT DOCUMENTS

| | | | |
|---|---|---|---|
| 4,765,669 A * | 8/1988 | Meier | B25J 13/082 294/106 |
| 5,509,707 A * | 4/1996 | Schauer | B23Q 7/043 294/119.1 |
| 6,196,504 B1 * | 3/2001 | Lemke | F16M 11/041 396/428 |
| 2006/0161138 A1 | 7/2006 | Orban, III et al. | |
| 2011/0015650 A1 | 1/2011 | Choi et al. | |
| 2011/0146128 A1 * | 6/2011 | Haering | F41G 11/003 42/90 |
| 2012/0308301 A1 * | 12/2012 | Walsch | B25J 15/0408 403/361 |
| 2013/0103051 A1 | 4/2013 | Cooper et al. | |
| 2015/0366621 A1 | 12/2015 | Wang | |
| 2016/0242861 A1 | 8/2016 | Flatt et al. | |
| 2020/0061847 A1 * | 2/2020 | Dixon | A61B 34/70 |

OTHER PUBLICATIONS

Int'l Search Report for PCT/US2017/064164, dated Feb. 28, 2018.

* cited by examiner

*Primary Examiner* — Vicky A Johnson
(74) *Attorney, Agent, or Firm* — MaxGoLaw PLLC (57) ABSTRACT

A coupling device is described herein for coupling two objects. The coupling device includes a body having a receiving member, a bore, and a locking pin situated inside the bore. The locking pin is translatable beyond the bore to intercept a portion of an attachment region of an object to removably couple the object to the coupling device. A lever connected to the locking pin allows a user to rotate the locking pin. Upon rotation of the lever, components in the body cause the locking pin to rotate and translate towards the object to intercept the portion of the attachment region of the object.

20 Claims, 11 Drawing Sheets

QUICK RELEASE COUPLER

RELATED APPLICATIONS

This application is a continuation-in-part of U.S. application Ser. No. 16/467,756 filed Jun. 7, 2019; that in turn claims priority benefit of U.S. Provisional Application Ser. No. 62/433,373 filed Dec. 13, 2016; the contents of the aforementioned are hereby incorporated by reference.

TECHNICAL FIELD

The present invention in general relates to the field of mechanical couplers for connecting tools to a machine, and more specifically to a quick-release mechanical coupler for connecting tools to a surgical robot.

BACKGROUND

Couplers, or couplings, are commonly used to connect tools to machines. In some instances, couplers are configured with a quick release mechanism to rapidly release and connect tools to a machine, and are referred to as a quick-release coupler. A quick-release coupler is especially useful in situations where several tools are needed to connect to a single machine to perform a given task, or where the time for completing a given task is a matter of interest. These situations are often encountered in the field of surgical robotics where one or more tools need to be connected to the end of a robotic arm.

Due to the strict safety and accuracy requirements to perform robotic surgery, any coupler used during the procedure must meet several requirements. For one, the tools need to rigidly connect to the surgical robot such that there is minimal deflection between the tool and the robot. Often, a calibration step is performed prior to executing the procedure to identify the position and orientation of the tool tip, or working portion of the tool, in a coordinate frame of the robot. If the tool deflects after this calibration step, then the accuracy of the procedure is compromised. Second, the coupler connection needs to withstand the forces generated between the tool and the workpiece as well as any vibrational motion the robot may generate during the procedure. Like before, maintaining the rigidity between the tool and the robot is critical.

In addition, a surgical setting has sterility requirements where all of the components that directly interact with a patient must be sterile. Some quick-release couplers contain several small moving parts to firmly grasp the tool, which may be difficult to fully sterilize. A sterile drape may cover and shield the quick-release coupler from the patient, however the drape may inadvertently interact with any of the levers on the coupler used to connect and release the tool with the robotic arm.

Finally, the quick-release coupler has to account for the manufacturing tolerances between the coupler and the tool connection interface. More specifically, each tool has an attachment member that connects with the coupler. The attachment member for each tool may have a slightly different size, shape, or geometry due to the designated manufacturing tolerance (e.g., +/−0.5 mm). Therefore, the coupler design should accommodate for the minor variances in shape, size, or geometry from tool to tool due to the manufacturing tolerances, such that the rigidity between the robot and the different tools is maintained.

Thus, there exists a need for a quick-release coupler capable of connecting several types of tools to a robot and to maintain the rigidity between the tool and the robot during a surgical procedure.

SUMMARY

A coupling device is provided herein. The coupling device includes a body having a mounting member and a receiving member. The mounting member is attached to the body with a first set of fastening elements. The receiving member is attached to an opposing side of the body with a second set of fastening elements. The mounting member is adapted to connect to a portion of a machine and the receiving member is adapted to removably join and suspend one or more different tools. The portion of the machine may include a distal link of a manipulator arm of a robot. The receiving member further includes a conduit and a support where the conduit provides a link for a locking pin to intercept a portion of the tool. The support may be a sliding joint that is tapered with where an opening of the sliding joint has a larger cross-section than a stopper portion of the joint. The stopper portion provides an abutment surface for a corresponding mating feature of the tool to push against to rigidly secure the tool to the coupler. The corresponding mating feature may be a wedged attachment that slides onto the receiving member. The wedged attachment further includes an interaction counterbore bored through a top side of a portion of the wedged attachment. A wall in the interaction counterbore interacts with the locking pin such that when the locking pin is engaged the locking pin imposes a lateral force on the wall to rigidly secure the tool against the support of the coupler.

The body of the coupling device may further include a housing, a locking pin, a lever, a lid, one or more pawls, one or more pawl springs, a pawl release, a release button, a release lever, a biasing spring, one or more translation pins, a set screw, and fastening elements. The housing has a housing counterbore to hold the locking pin therein and a slot extending laterally from the housing counterbore through a portion of the housing. The lever fits within the slot and has an attachment end that inserts into a corresponding aperture in a shaft portion of the locking pin. The lever is used to rotate the locking pin within the counterbore to engage the tool.

A process of using the coupling device is provided including attaching a tool to the coupling device.

A system is also provided including a robot with a manipulator arm joined to the coupling device for removably joining a set of tools.

BRIEF DESCRIPTION OF THE DRAWINGS

The present invention is further detailed with respect to the following drawings that are intended to show certain aspects of the present of invention, but should not be construed as a limit on the practice of the invention, wherein:

FIGS. 2A and 2B depict a coupler for connecting a tool to a machine, where

FIGS. 3A-3C depict a mounting member of the coupler of FIGS. 2A and 2B that connects with a machine, where FIG.

3A is a perspective view of the mounting member, FIG. 3B is a top view thereof, and FIG. 3C is a side view thereof in accordance with embodiments of the invention;

FIGS. 4A-4D depict a receiving member of the coupler of FIGS. 2A and 2B that receives a tool, where

FIGS. 5A-5D depict an attachment region and a tool for attaching with the receiving member of FIGS. 4A-4D, where

FIGS. 7A-7E depict detailed perspective views of the locking pin shown in FIG. 6 that secures a tool to the coupler, where FIG. 7A is a perspective view of the locking pin.

FIGS. 8A-8D depict detailed perspective views of the lid shown in FIG. 6 of the coupler that facilitates a translational motion of the locking pin, where FIG. 8A is a top view of the lid.

FIGS. 13A-13B are top down views of the pawl release mechanism of FIG. 10, where

FIGS. 14A-14B depict a bottom surface of the coupler body for assembling the pawl release mechanism, where FIGS. 15A-15B depict a cross-sectional view of the assembled coupler of FIG. 2A, where

DETAILED DESCRIPTION

The present invention has utility as a mechanical coupler to quickly and rigidly connect a tool to a machine. The mechanical coupler is especially advantageous in a surgical setting where time is of the essence and where a single machine operates different tools at different time points to perform a single procedure. Further, the mechanical coupler is capable of connecting tools having small geometric deviations in their attachment regions, while still providing a rigid connection between the machine and the tool.

The following description of the various embodiments of the invention is not intended to limit the invention to these specific embodiments, but rather to enable any person skilled in the art to make and use the invention through exemplary aspects thereof. In particular, the following description provides examples related to a coupler for connecting a tool to a surgical robot; however, it should be appreciated that the embodiments described herein are readily adapted for use in a myriad of applications where it is desirous to connect two or more objects.

It is to be understood that in instances where a range of values are provided that the range is intended to encompass not only the end point values of the range, but also intermediate values of the range as explicitly included within the range and varying by the last significant figure of the range. By way of example, a recited range from 1 to 4 is intended to include 1-2, 1-3, 2-3, 2-4, 3-4, and 1-4.

Figure 1:
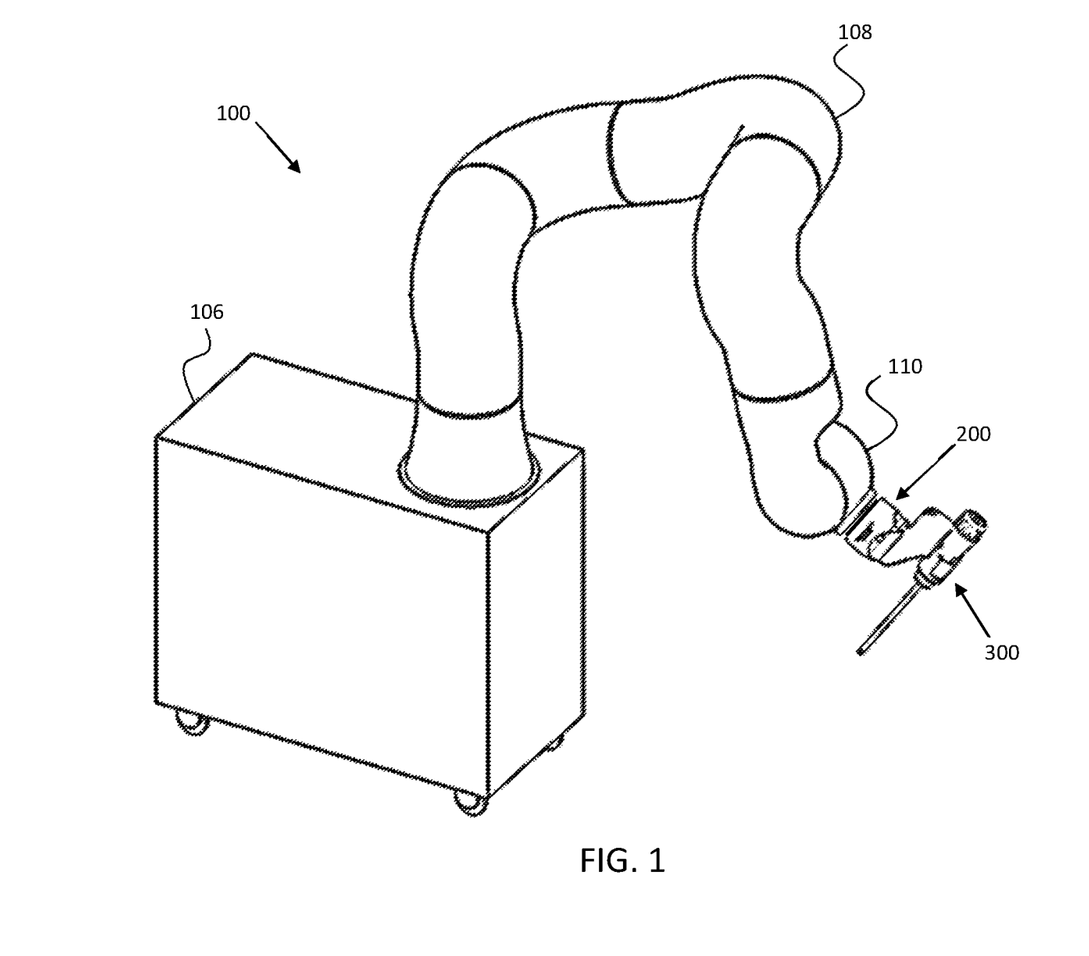
FIG. 1 depicts a robotic system having a coupler and a tool attached thereto in accordance with embodiments of the invention.

Referring now to the figures, FIG. 1 illustrates a robotic system 100 including a robot base 106, a manipulator arm 108 mounted to the base 106 having a distal link 110, a mechanical coupler 200 connected to the distal link 110, and a tool 300 attached to the coupler 200. FIG. 1 is provided for context as a potential application for the use of the mechanical coupler 200 described herein. In particular, the robotic system 100 may perform orthopedic procedures such as total knee arthroplasty (TKA) and total hip arthroplasty (THA) where several different tools are used by the robotic system during the course of a single procedure. One specific example is the reaming of the acetabular cup during THA where several reamers are exchanged on the robotic arm 108 to prepare the acetabulum to receive a prosthetic cup. Examples of such robotic systems are described in U.S. Pat. Nos. 5,086,401, 6,102,850 and 7,206,626, which are incorporated by reference herein in their entirety.

Figure 2A:
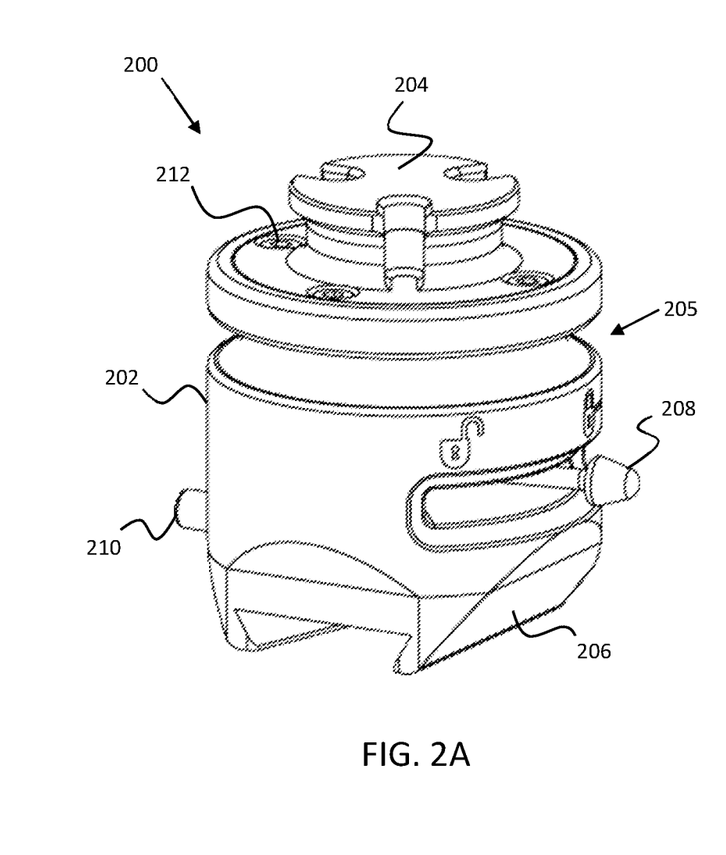
FIG. 2A shows the coupler in an assembled state.
Figure 2B:
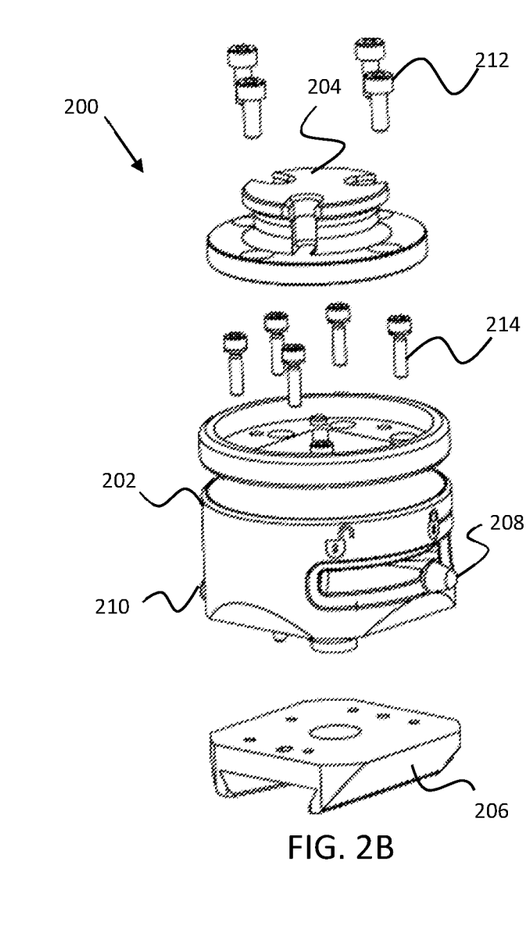
FIG. 2B shows an exploded view thereof in accordance with embodiments of the invention.

With reference to FIGS. 2A and 2B, the mechanical coupler 200 is shown, where FIG. 2A is a perspective view of the coupler 200 and FIG. 2B is an exploded view thereof. The coupler 200 includes a body 202 having a mounting member 204 and a receiving member 206. The mounting member 204 is assembled to the body 202 with a first set of fastening elements 212, while the receiving member 206 is assembled to an opposing side of the body 202 with a second set of fastening elements 214. The fastening elements (212, 214) shown here are screws, however other fastening elements may be used such as clamps, rivets, screw caps, and equivalents thereof.

Figures 3A, 3B, 3C:
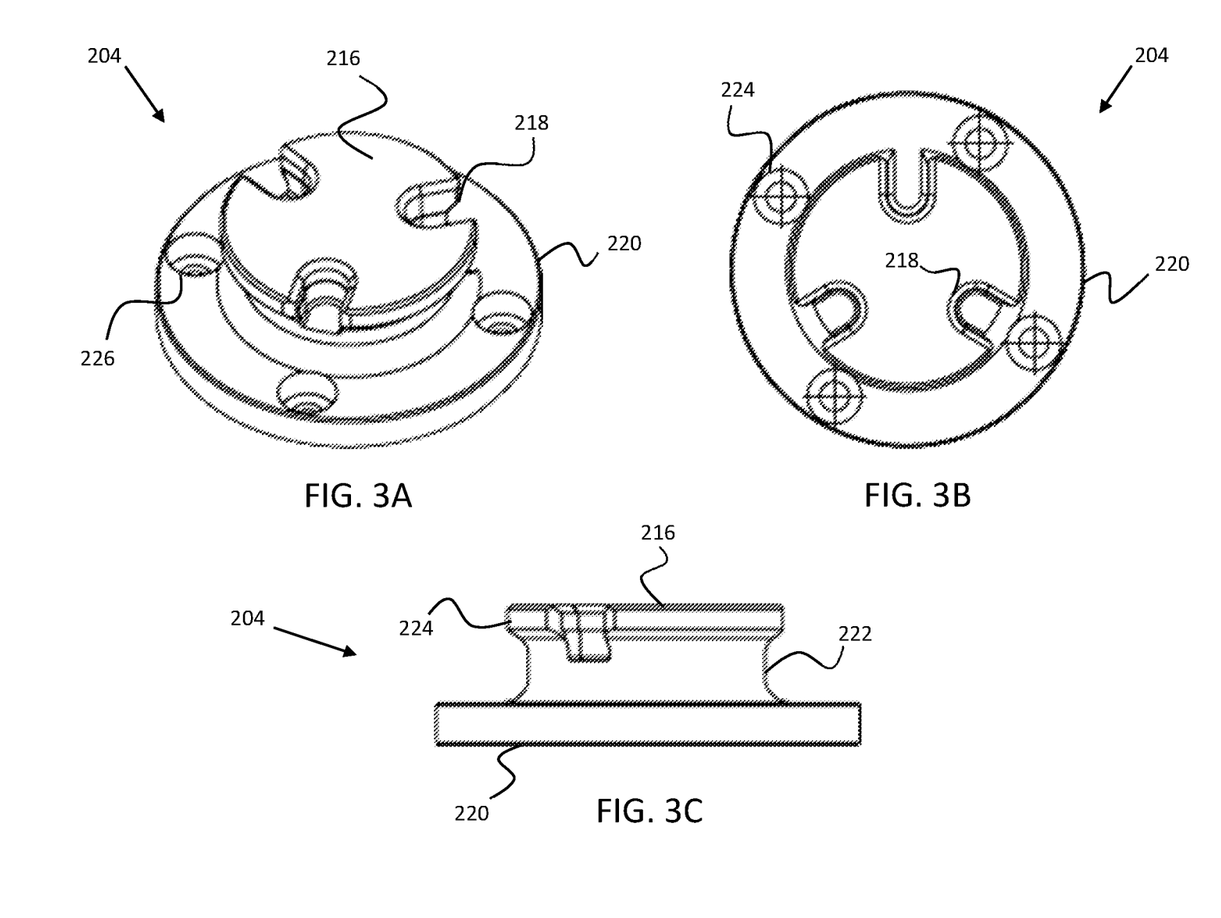

With reference to FIGS. 3A-3C, the mounting member 204 is shown in detail, where FIG. 3A is a perspective view of the mounting member 204, FIG. 3B is a top view thereof, and FIG. 3C is a side view thereof. The mounting member 204 is adapted to connect to a portion of a machine, such as the distal link 110 of the manipulator arm 108. In a particular embodiment, the mounting member 204 has an annular base 220 and a cylindrical top 216 with a hyperboloid neck 222 therebetween. The top 216 and neck 222 having diameters less than the annular base 220 for inserting inside a locking mechanism (not shown) associated with the machine. One or more alignment slots 218 may be formed around the edge of the cylindrical top 216 to mate with one or more corresponding projections associated with the locking mechanism of the machine. The alignment slots 218 ensure the coupler 200 may be repeatedly connected to the machine in a desired orientation. The neck 222 may be securely grasped by a set of retractable ball bearings associated with the machine locking mechanism to rigidly fix the coupler 200 to the machine. In addition, the annular base 220 may further include a set of screw holes 226 to receive the set of fastening elements 212 to assemble the mounting member 204 with the body 202.

In other embodiments, the mounting member 204 may have alternative mechanisms known in the art for connecting the coupler 200 to the machine. For example, the mounting member 204 may have a shaft with threads that screw into a portion of the machine, a clamping mechanism, or equivalents thereof to maintain a rigid relationship between the machine and the mounting member 204. It is further contemplated that the coupler 200 may be a permanently assembled or manufactured as part of the machine (or other object). In this case, the coupler 200 may not include a mounting member 204, or the mounting member 204 may be permanently assembled to the machine.

Figure 4A:
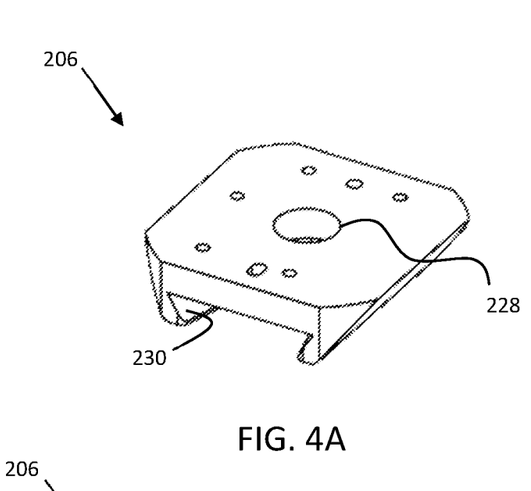
FIG. 4A is a perspective top view of the receiving member.
Figure 4B:
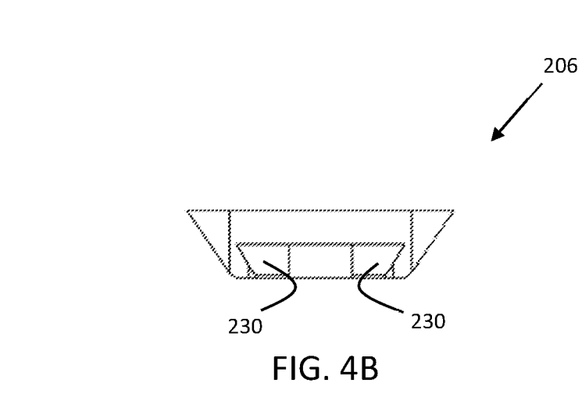
FIG. 4B is a front view thereof.
Figure 4C:
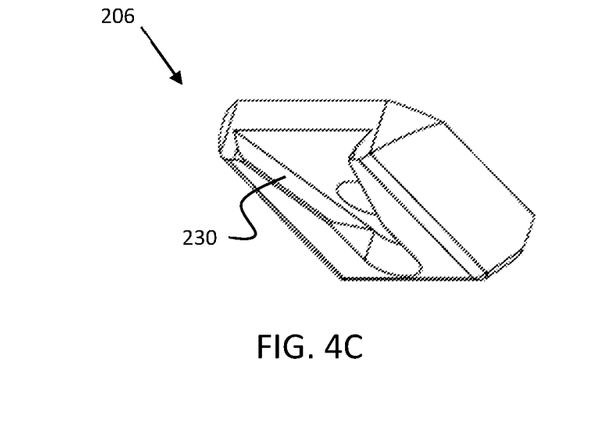
FIG. 4C is a perspective bottom view thereof.
Figure 4D:
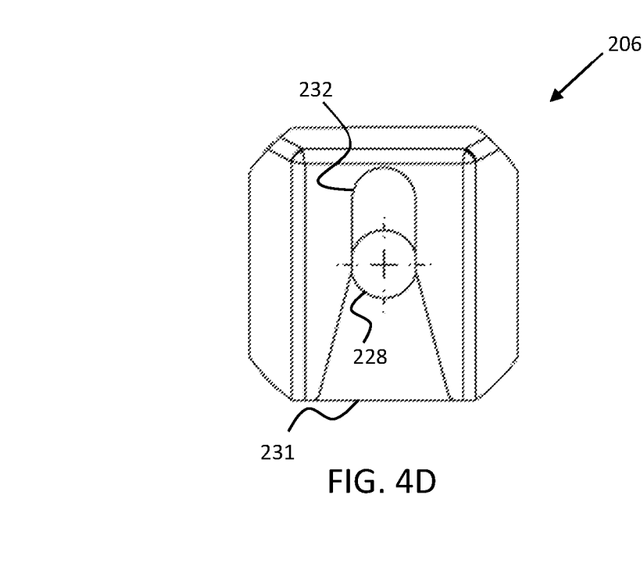
FIG. 4D is a bottom view thereof.

With reference to FIGS. 4A-4D the receiving member 206 of the body 202 is shown in detail, where FIG. 4A is a top perspective view of the receiving member 206, FIG. 4B is front view thereof, FIG. 4C is a bottom perspective view thereof, and FIG. 4D is a bottom view thereof. The receiving member 206 is adapted to removably join and suspend the tool 300 to the coupler 200. In a particular embodiment, the receiving member 206 has a conduit 228 and a support 230. The conduit 228 provides a link for a locking pin 236 (shown in FIG. 6) to intercept a portion of the tool 300 as described below. The support 230 is adapted to mate with the tool 300. In a specific embodiment, the support 230 is a sliding joint (e.g., "stopped" sliding dovetail joint) that mates with a corresponding mating feature on the tool 300. The sliding joint may be tapered where an opening 231 of the joint has a larger cross-section than the "stopped" portion 232 of the joint. The "stopped" portion 232 may provide an abutment surface for the corresponding mating feature on the tool to push against to rigidly secure the tool 300 to the coupler 200 as further described below. It should be appreciated, that the "stopped" portion 232 refers to any portion of the joint that extends away from the opening 231 where the corresponding mating feature on the tool 300 may push against any region of the "stopped" portion 232 (e.g., the side walls of the dovetail joint may act as the abutment surface, where the mating feature may push against the side walls of the dovetail joint without contacting a region of the "stopped" portion 232 furthest from the opening 231). In other embodiments, the support 230 may be a simple lip or slot that the tool 300 can mate with or slide onto for removably joining and suspending the tool 300.

Figure 5A:
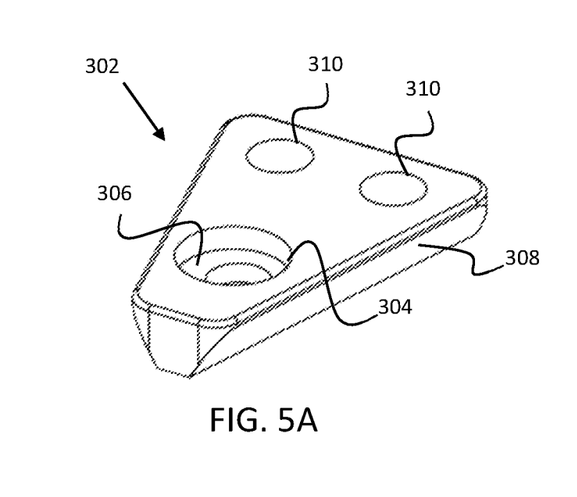
FIG. 5A is a perspective view of the attachment region.
Figure 5B:
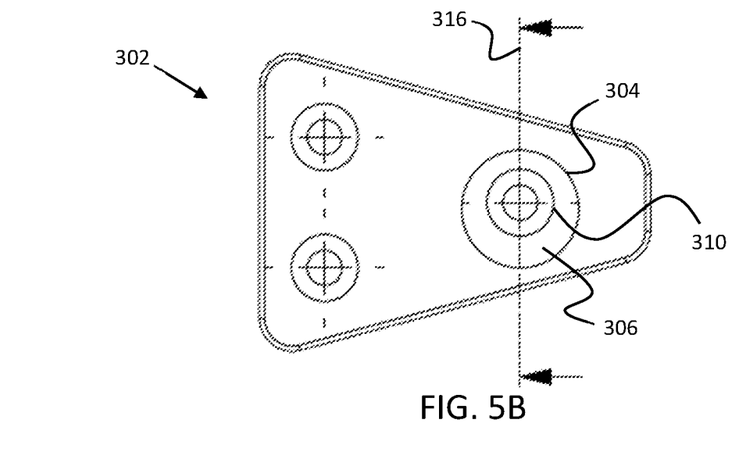
FIG. 5B is a top view thereof.
Figure 5C:
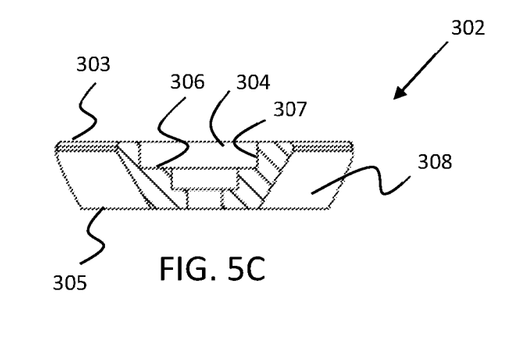
FIG. 5C is a front cross-sectional view thereof.
Figure 5D:
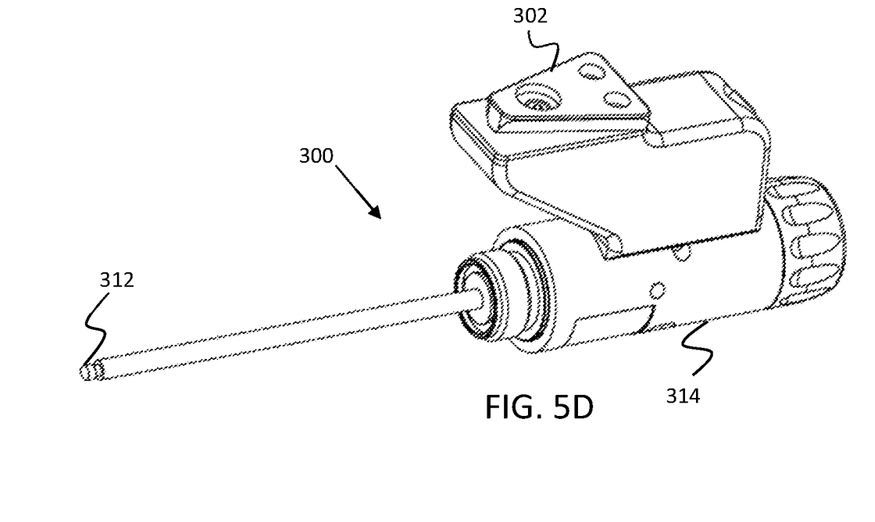
FIG. 5D is the attachment region assembled with a tool, in accordance with embodiments of the invention.

With reference to FIGS. 5A-5D, a tool 300 having a wedged attachment region 302 is shown in detail, where FIG. 5A is a perspective view of the attachment region 302, FIG. 5B is a top view of thereof, FIG. 5C is cross-sectional view thereof along line 316 of FIG. 5B, and FIG. 5D depicts the tool 300 having the attachment region 302. The attachment region 302 is adapted to mate and/or slide onto the receiving member 206. In a specific embodiment the attachment region 302 has a top surface 303, a bottom surface 305, and wedged angled features 308 therebetween that slide onto the support 230 (i.e., the dovetail joint). The attachment region 302 further includes a locking pin interaction feature 304. In a particular embodiment, the interaction feature 304 is in the form of a counterbore bored through a portion of the attachment region 302 leaving a counterbore interaction wall 307 and an interaction surface face 306 situated between the top surface 303 and the bottom surface 305. A locking pin 236 (shown in FIG. 6) engages the interaction feature 304 as further described below. The wedge-shaped attachment region 302 further includes fastening holes 310 for fastening elements to attach the attachment region 302 with the tool 300. In a specific embodiment, the tool 300 as shown in FIG. 5D is a powered cutter having a cutter tip 312 driven by a motor 314. However, it should be appreciated that the attachment region 302 may be assembled with any type of tool including but not limited to a reamer, a burr, an electrocautery device, a probe, an endoscope, a drill, a prosthetic implant, or any other instrument that interacts with a user, a workpiece, a subject, or the environment. In another embodiment, the coupler 200 is adapted to removably couple with a workpiece rather than a tool. The workpiece may include an attachment region that interacts with the receiving member 206 of the coupler 200. The workpiece may be, for example, a patient's anatomy (e.g., bone), wood, metals, polymers, or other objects that will undergo some type of processing, modification, or alteration.

Figure 6:
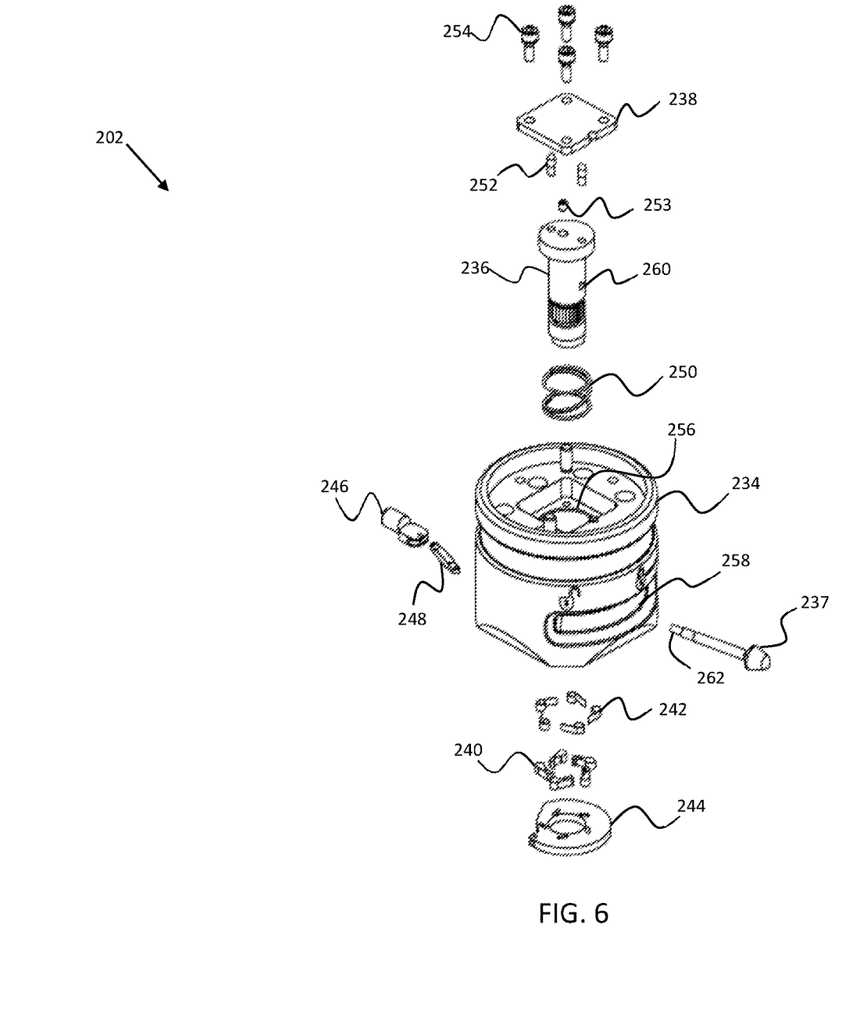
FIG. 6 is an exploded view of the body of the coupler of FIGS. 2A and 2B in accordance with embodiments of the invention.

With reference to FIG. 6, the body 202 of the coupler 200 is shown in an exploded view. The body 202 is configured to permit a user to engage and disengage a locking pin 236 with the interaction feature 304. When the user engages the locking pin 236, a portion of the locking pin 236 imposes a lateral force on the interaction feature 304 to rigidly secure the tool 300 against the support 230 of the coupler 200. In particular, the locking pin 236 imposes a lateral force on the interaction wall 307 to securely "wedge" and draw the attachment region 302 into the support 230 (i.e., wedged sliding joint). In a specific embodiment, the body 202 includes a housing 234, the locking pin 236, a lever 237, a lid 238, one or more pawls 240, one or more pawl springs 242, a pawl release 244, a release button 246, a release lever 248, a biasing spring 250, one or more translation pins 252, a set screw 253, and fastening elements 254. The housing 234 has a counterbore 256 to hold the locking pin 236 therein and a slot 258 extending laterally from the counterbore 256 through a portion of the housing 234. The lever 237 fits within the slot 258 and has an attachment end 262 that inserts into a corresponding aperture 260 in the shaft of the locking pin 236. The lever 237 allows the user to rotate the locking pin 236 within the counterbore 256. The lid 238 has features that cause the locking pin 236 to translate within the counterbore 256 as the locking pin 236 rotates to engage the tool 300.

Figure 7A:
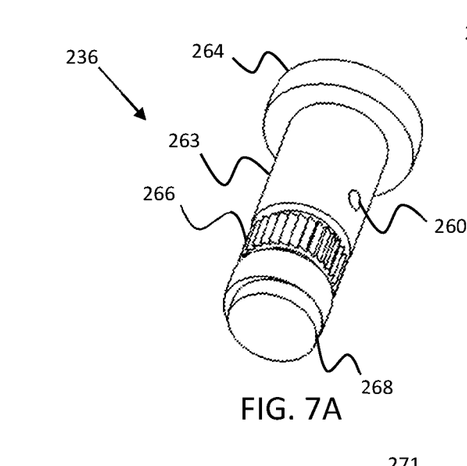
Figure 7B:
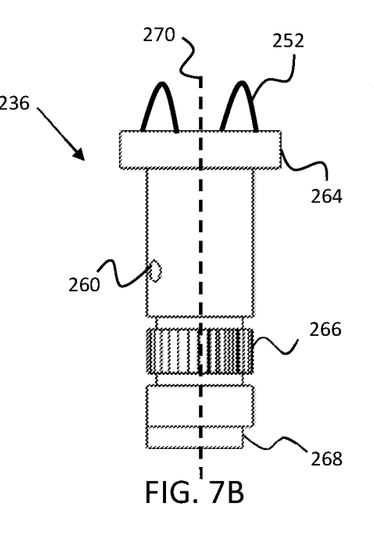
FIG. 7B is first rotational position thereof.
Figure 7C:
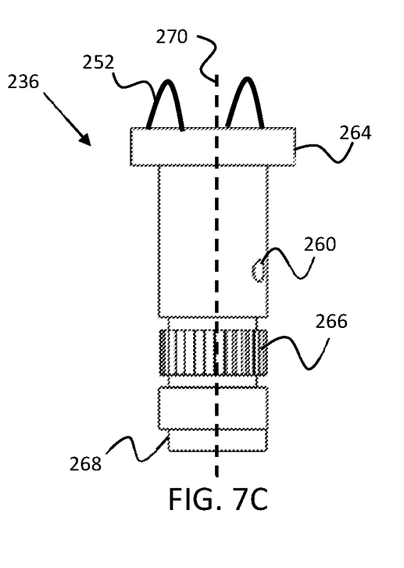
FIG. 7C is a second rotational position thereof.
Figure 7D:
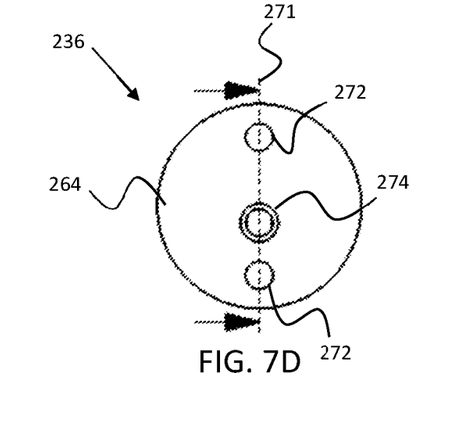
FIG. 7D is a top view thereof.
Figure 7E:
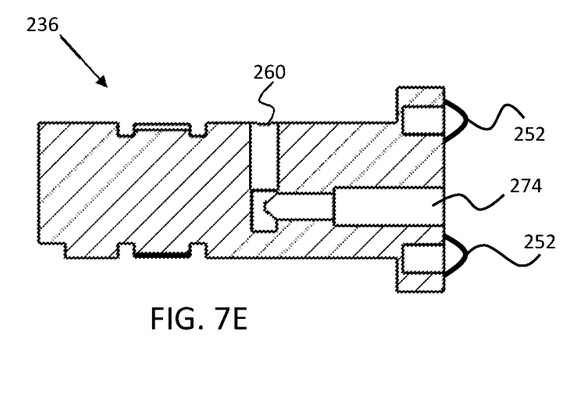
FIG. 7E is a cross-section view thereof, in accordance with embodiments of the invention.

With reference to FIGS. 7A-7E, the locking pin 236 is shown in detail, where FIG. 7A is a perspective view of the locking pin 236, FIG. 7B shows the locking pin 236 in a disengaged position, FIG. 7C shows the locking pin in an engaged position, FIG. 7D is a top view thereof, and FIG. 7E is a cross-section thereof along line 271 of FIG. 7D. In a particular embodiment, the locking pin 236 is a shaft 263 having a pin head 264 at a proximal end of the shaft 263, an aperture 260 for receiving the lever 237, a plurality of teeth 266 radially positioned on an outer surface of the shaft 263, and an eccentric cam 268 at a distal end of the shaft 236. The eccentric cam 268 is offset from the center axis 270 of the shaft 263 which applies a lateral force against the wall 307 of the attachment region 302 when the locking pin 236 is engaged. This can be viewed between FIGS. 7B and 7C, where FIG. 7B illustrates the locking pin 236 rotated in a disengaged position and FIG. 7C illustrates the locking pin 236 rotated in an engaged position. The plurality of teeth 266 engage with one or more pawls 240 to incrementally lock the rotational position of the locking pin 236 as the locking pin 236 is rotated. The plurality of teeth 266 may be manufactured as a part of the locking pin 236, as a sprocket, or a removable set of teeth may be attached thereto. The locking pin 236 further include translation pins 252 projecting from the pin head 264 and a channel 274 where the set screw 253 (as shown in FIG. 6) is inserted and screwed against the attachment end 262 of the lever 237 to secure the lever 237 to the locking pin 236.

Figure 8A:
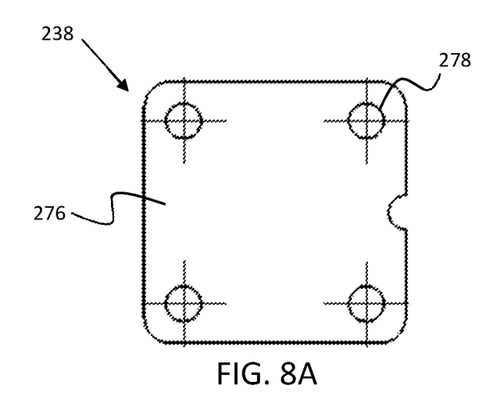
Figure 8B:
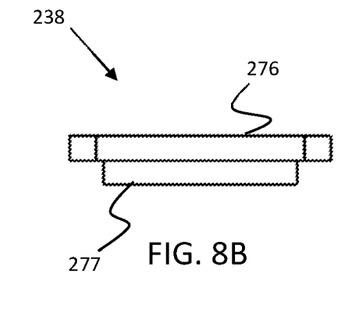
FIG. 8B is side view thereof.
Figure 8C:
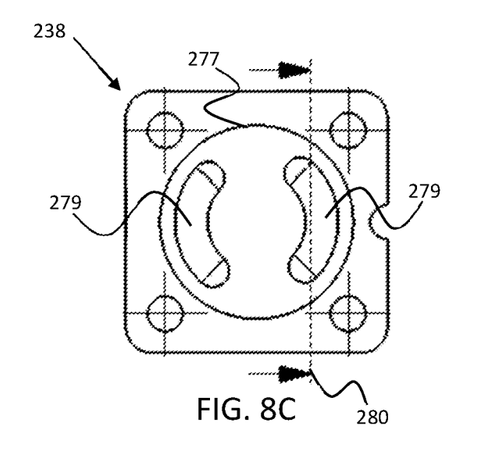
FIG. 8C is bottom view thereof.
Figure 8D:
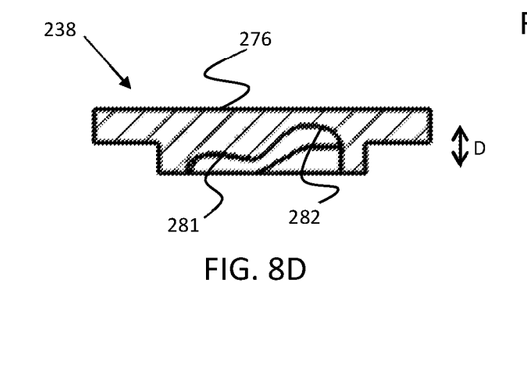
FIG. 8D is a cross-sectional view thereof in accordance with embodiments of the invention.
Figure 9:
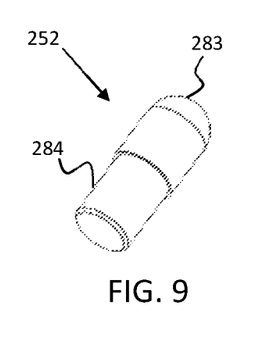
FIG. 9 depicts a detailed perspective view of the translational pin shown in FIG. 6 that interacts with the lid in accordance with embodiments of the invention.
Figure 10:
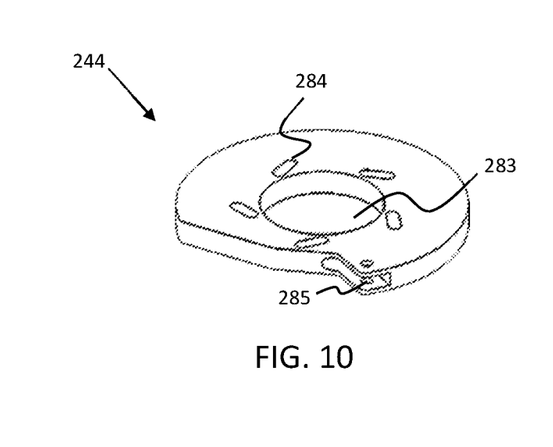
FIG. 10 depicts a detailed perspective view of the pawl release shown in FIG. 6 that facilitates the release of a pawl from the locking pin in accordance with embodiments of the invention.

With reference to FIGS. 8A-8D, the lid 238 is shown in detail, where FIG. 8A is a top view of the lid 238, FIG. 8B is a side view thereof, FIG. 8C is a bottom view thereof, and FIG. 8D is a cross-section thereof through line 280 of FIG. 8C. The lid 238 is configured to cause the locking pin 236 to translate as the locking pin 236 is rotated. In a particular embodiment, the lid 238 has a top portion 276, and a bottom portion 277. The bottom portion 277 has a cylindrical shape with two grooves 279. The grooves 279 interact with the translation pins 252 that project from the locking pin 236. In particular, the translation pins 252 (as shown in FIG. 9) have a dome portion 283 that fit into the grooves 279 and a press-fit portion 284 that attach with the pin head 264 of the locking pin 236. The inside of each groove 279 has an undulating surface as seen in FIG. 8D. One side of the groove 281 has a surface lower than the opposite side 282 by a distance 'D'. As the locking pin 236 is rotated, the undulating surface makes the locking pin 236 translate.

Figure 11:
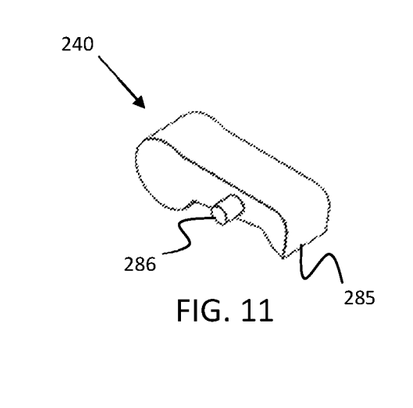
FIG. 11 depicts a detailed perspective view of the pawl shown in FIG. 6 that engages the locking pin in accordance with embodiments of the invention.
Figure 12:
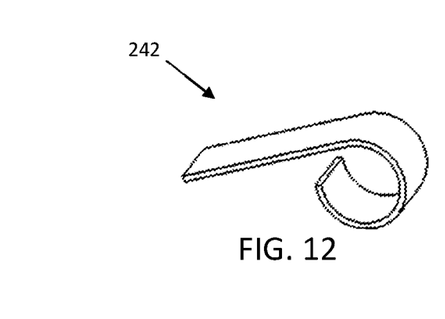
FIG. 12 depicts a detailed perspective view of the pawl spring shown in FIG. 6 that interacts with the pawl in accordance with embodiments of the invention.
Figure 13A:
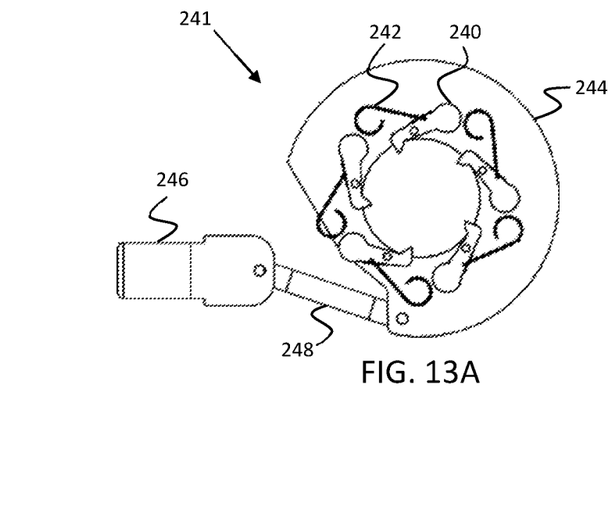
FIG. 13A shows the pawl release mechanism in an engaged position and FIG. 13B is in a disengaged position in accordance with embodiments of the invention.
Figure 13B:
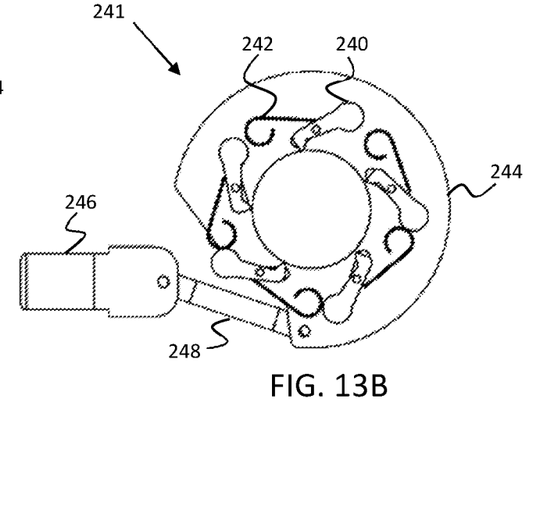

With reference to FIGS. 10-13B, a mechanism for incrementally locking a rotational position of the locking pin 236 and releasing the lock is shown in detail. The pawl release mechanism 241 is configured to disengage the pawls from the plurality of teeth 266 on the locking pin 236. In particular embodiment, the pawl release 244 is of a semi-annular shape having one or more pawl engagement features 284, a conduit 283, and a release lever attachment point 285. The pawl engagement feature(s) 284 may be an angled elliptical opening that receives a portion of the pawl 240. For example, as shown in FIG. 11, the one or more pawls 240 have an engaging element 285 for engaging the plurality of teeth 266 and a pin 286 that fits within the pawl engagement feature 284. One or more pawl spring 242, as shown in FIG. 12, is configured about each of the pawls 240 such that the pawls 240 can engage each of the teeth 266 as the locking pin 236 is rotated. To release the pawl(s) 240 from the teeth 266, a user pushes on a release button 246 connected to a release lever 248 that is connected to the pawl release 244. Pushing the release button 246 rotates the pawl release 244 causing each of the pawls to rotate away from the teeth 266. The pawls rotate because the pin 286 moves within the pawl engagement feature 284 (e.g., an angled elliptical opening) angled away from the teeth 266. FIG. 13A depicts the pawl(s) 240 in the engaged position, and FIG. 13B depicts the pawl(s) 240 in the disengaged position due to the rotation of the pawl release 244.

There are several advantages of having multiple pawls 240, including the ability to increase the locking resolution of rotation. In a particular inventive embodiment, the spacing of the plurality of teeth 266, the positioning of the pawls 240 around the teeth 266, and the number of pawls 240, is configured such that only one or two pawls 240 are engaged with one or two teeth at any given rotational position. Therefore, the slightest rotation will cause one or two other pawls 240 to engage one or two other teeth 266. This configuration provides several additional advantages. For one, when manufacturing the attachment region 302 of the tool 300, the geometry of each attachment region may vary slightly due to manufacturing tolerance. The several locking positions and resolution of locking accommodates for these slight variations for each tool 300 used with the machine. Second, by having several locking positions, the risk of the tool 300 detaching from the coupler 200 is greatly reduced because there are several "stops" before the tool 300 can be fully detached. In addition, with a coupler having only one pawl 240 or one locking position (as opposed to the multiple paws 240 described herein), unintended external forces (e.g., a surgical drape surrounding the coupler, vibrations or motions of the machine or robot, or a user bumping the coupler 200), may snag the lever 237 and inadvertently release the tool 300 from the coupler 200. Therefore, several locking positions also provide several degrees of connection security.

Figure 14A:
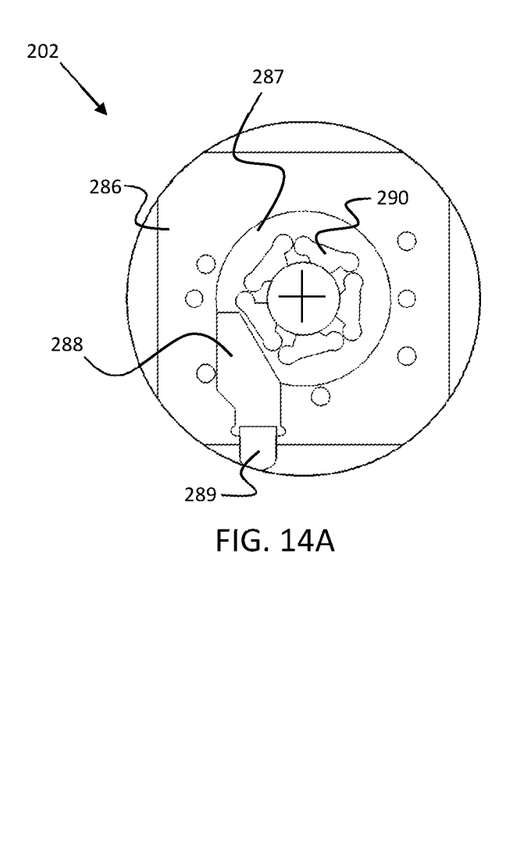
FIG. 14A is the bottom surface having no pawl release components and FIG. 14B is the assembled pawls and springs with the body in accordance with embodiments of the invention.
Figure 14B:
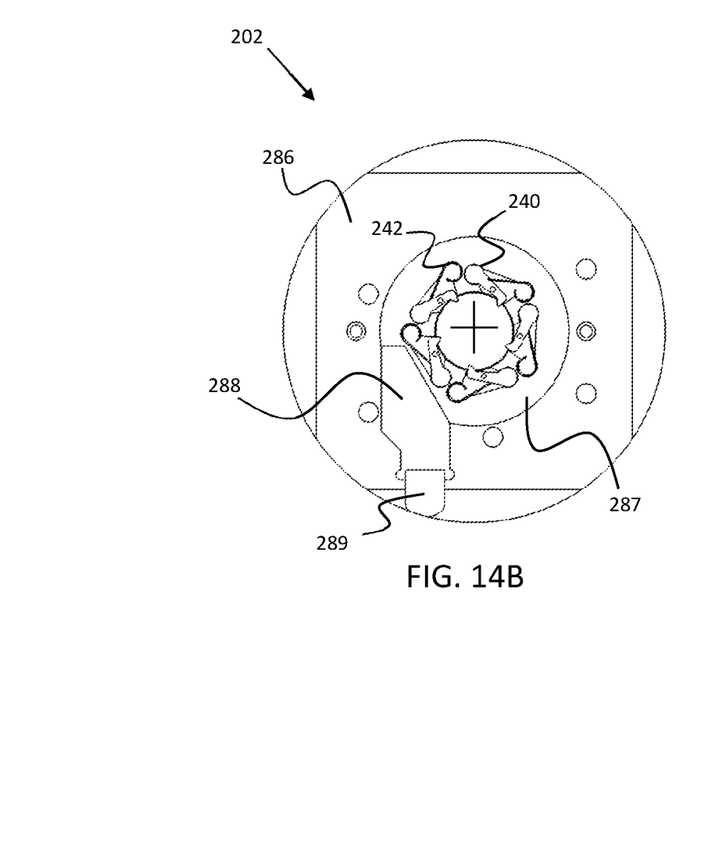

With reference to FIG. 14A, a bottom surface 286 of the body 202 (see FIG. 6) is shown. The bottom surface 286 is adapted to receive and assemble the pawl release mechanism 241. In a particular embodiment, the bottom surface 286 is manufactured having a pawl release recession 287 to receive the pawl release 244, a release lever recession 288 to receive the release lever 248, a release button recession 289 to receive the release button, and a pawl and spring recession 290 to receive and assemble the pawls 240 and pawl springs 242. FIG. 14B shows the pawls 240 and springs 242 assembled with the body 202.

Figure 15A:
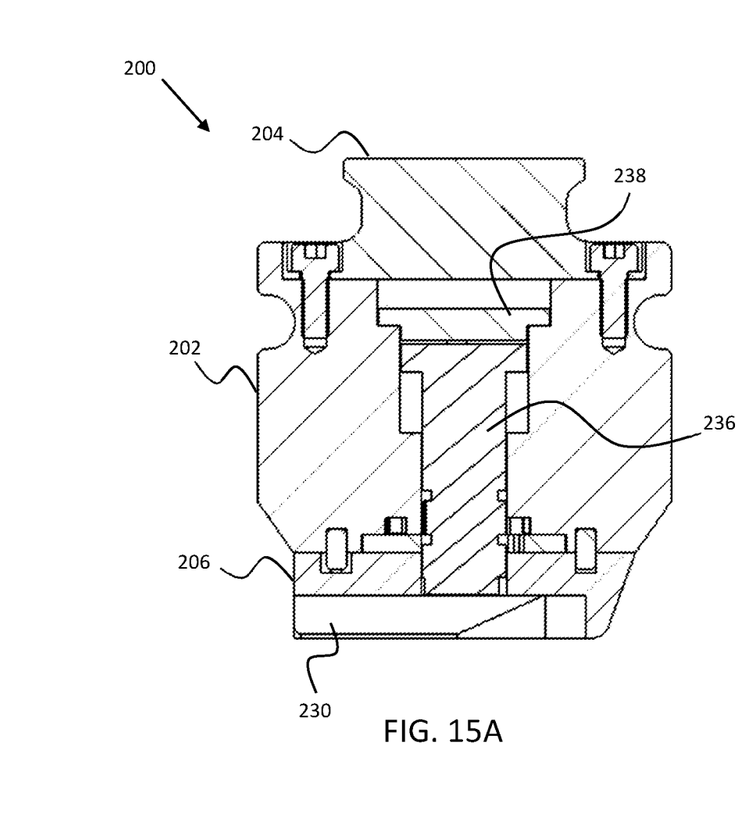
FIG. 15A is the coupler in a disengaged position and FIG. 15B is the coupler in an engaged position in accordance with embodiments of the invention.
Figure 15B:
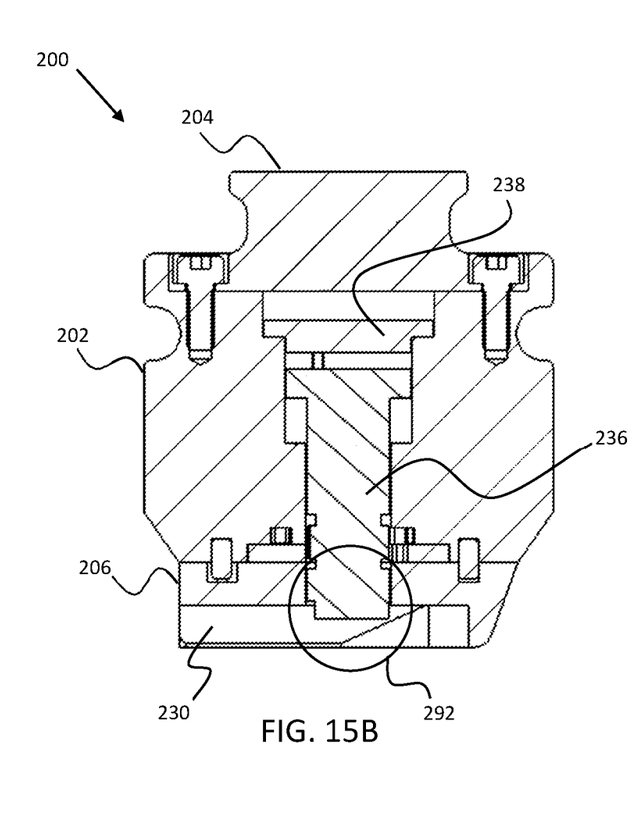

With reference to FIG. 15A-15B a cross-section of the assembled coupler 200 is shown. FIG. 15A shows the coupler 200 in a disengaged position where the locking pin 236 is fully housed within the body 202 and the conduits (228, 283) of the receiving member 206 and pawl release 244. In this position, the attachment region 302 of the tool 300 can slide onto the support 230 where the tool 300 is now suspended thereon. To rigidly secure the tool 300 to the coupler 200, the user rotates the lever 237 causing the locking pin 236 to rotate and translate towards and against the locking pin interaction feature 304 of the attachment region 302 (see FIGS. 5A-5D). The locking pin 236 applies a lateral force (the lateral force is aided by the eccentric cam 268 of the locking pin 236) against the interaction feature 304 which pulls the tool 300 into the support 230 to rigidly and securely lock the tool 300 to the coupler 200. FIG. 15B shows the coupler 200 in the engaged position where the locking pin 236 extends partially within the support 230 as depicted in the circled region 292. To release the tool 300 from the coupler 200, the user presses the release button 246 to disengage the pawls and rotates the lever 237 back to the disengaged position where the biasing spring 250 (see FIG. 6) aids in translating the pin 236 back into the body 202. The user can then slide the tool 300 off the support 230 and assemble another tool 300 thereto if needed quickly and effectively.

In a particular embodiment, with reference back to FIG. 2A, the body 202 further includes a groove 205 to facilitate the assembly of a sterile drape to the machine. The sterile drape may have a tubular form to encapsulate a portion of the machine (e.g., an arm of a surgical robot) and provide a sterile barrier to the environment. One end of the sterile drape may be configured to slip into the groove 205 of the body 202 to easily assemble that end of the sterile drape to the coupler 200. The end of the sterile drape may be elastic to conform and hold the end of the sterile drape in the groove 205. This may alleviate the need to use adhesives to attach the sterile drape to the machine. The use of the groove 205 also ensures the end of the sterile drape remains on the coupler 200 and prevents the drape from sliding off of the coupler 200 and into the workspace. One example of a sterile drape for a surgical robot is described in U.S. patent application Ser. No. 15/744,253 assigned to the assignee of the present application and incorporated by reference herein.

Other Embodiments

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient roadmap for implementing the exemplary embodiment or exemplary embodiments. It should be understood that various changes may be made in the function and arrangement of elements without departing from the scope as set forth in the appended claims and the legal equivalents thereof.

The invention claimed is:

1. A coupling device, comprising:
   a body comprising:
      a receiving member adapted to be removably coupled with an attachment region of a separate first object; and
      a bore located within a portion of the body;
   a locking pin positioned in the bore and axially translatable beyond the bore to intercept a portion of the attachment region when the attachment region is coupled to the receiving member; and
   a lever for rotating the locking pin.

2. The coupling device of claim 1 wherein the receiving member further comprises a support for mating with the attachment region.

3. The coupling device of claim 2 wherein the support is a dovetail joint comprising an opening and a stop portion.

4. The coupling device of claim 1 wherein the body further comprises a slot extending from the bore to an outer surface of the body, wherein the lever fits within the slot.

5. The coupling device of claim 1 wherein the locking pin further comprises one or more pins, and wherein the coupling device further comprises a lid having a plurality of grooves that interact with the one or more pins to cause the locking pin to translate beyond the bore when the locking pin is rotated.

6. The coupling device of claim 5 wherein the grooves have an undulating surface.

7. The coupling device of claim 1 wherein the first object comprises at least one of a tool or a workpiece.

8. The coupling device of claim 1 wherein the locking pin further comprises a cam at a distal end of the shaft.

9. A system, comprising:
   a first object; and
   the coupling device of claim 1 mounted to a portion of the first object.

10. The system of claim 9 wherein the first object is a surgical robot.

11. The system of claim 9 further comprising a second object having an attachment region for removably coupling the second object to the coupling device.

12. The system of claim 11 wherein the attachment region comprises an interaction bore that interacts with the locking pin.

13. The system of claim 11 wherein the second object comprises at least one of a tool or a workpiece.

14. A coupling device, comprising:
   a body comprising:
      a receiving member adapted to be removably coupled with an attachment region of a separate first object; and
      a bore located within a portion of the body;
   a locking pin positioned in the bore and axially translatable beyond the bore to intercept a portion of the attachment region when the attachment region is coupled to the receiving member; and
   wherein the locking pin further comprises a shaft and a plurality of teeth radially positioned on an outer surface of the shaft, wherein one or more pawls engage one or more teeth of the plurality of teeth.

15. The coupling device of claim 14 further comprising a pawl release mechanism for disengaging the one or more pawls from the one or more teeth.

16. The coupling device of claim 15 wherein the pawl release mechanism comprises one or more openings for receiving a portion of the one or more pawls, respectively, and a release lever.

17. The coupling device of claim 14 further comprising a lever for rotating the locking pin.

18. A coupling device, comprising:
   a body comprising:
      a receiving member adapted to be removably coupled with an attachment region of a separate first object; and
      a bore located within a portion of the body;
   a locking pin positioned in the bore and axially translatable beyond the bore to intercept a portion of the attachment region when the attachment region is coupled to the receiving member; and
   a mounting member adapted to mount the coupling device to a portion of a surgical robot.

19. The coupling device of claim 18 wherein the mounting member is located on a first side of the body and the receiving member is located on an opposing side of the body.

20. The coupling device of claim 18 further comprising a lever for rotating the locking pin.

* * * * *